US009519755B2

(12) United States Patent
Saalasti et al.

(10) Patent No.: US 9,519,755 B2
(45) Date of Patent: Dec. 13, 2016

(54) METHOD AND SYSTEM FOR EVALUATING A PHYSIOLOGICAL STATE DEPICTING A PERSON'S RESOURCES

(71) Applicant: FIRSTBEAT TECHNOLOGIES OY, Jyvaskyla (FI)

(72) Inventors: Sami Saalasti, Jyvaskyla (FI); Joni Kettunen, Jyvaskyla (FI); Satu Tuominen, Jyvaskyla (FI); Jaakko Kotisaari, Jyvaskyla (FI)

(73) Assignee: Firstbeat Technologies Oy, Jyväskylä (FI)

( * ) Notice: Subject to any disclaimer, the term of this patent is extended or adjusted under 35 U.S.C. 154(b) by 212 days.

(21) Appl. No.: 14/353,126

(22) PCT Filed: Nov. 9, 2012

(86) PCT No.: PCT/FI2012/051094
§ 371 (c)(1),
(2) Date: Apr. 21, 2014

(87) PCT Pub. No.: WO2013/068650
PCT Pub. Date: May 16, 2013

(65) Prior Publication Data
US 2014/0288448 A1  Sep. 25, 2014

Related U.S. Application Data

(60) Provisional application No. 61/629,564, filed on Nov. 22, 2011.

(30) Foreign Application Priority Data

Nov. 11, 2011  (FI) .................................... 20116115

(51) Int. Cl.
*A61B 5/00* (2006.01)
*G06F 19/00* (2011.01)
(Continued)

(52) U.S. Cl.
CPC ......... *G06F 19/3431* (2013.01); *A61B 5/0022* (2013.01); *A61B 5/02405* (2013.01);
(Continued)

(58) Field of Classification Search
USPC .................................................. 600/300–301
See application file for complete search history.

(56) References Cited

U.S. PATENT DOCUMENTS 5,755,671 A    5/1998 Albrecht et al.
7,330,752 B2   2/2008 Kettunen et al.
(Continued)

FOREIGN PATENT DOCUMENTS

WO   2004/016172   2/2004
WO   2004/047624   6/2004
(Continued)

OTHER PUBLICATIONS

International Preliminary Report on Patentability in corresponding PCT application No. PCT/FI2012/051094.

*Primary Examiner* — Nicole F Johnson
(74) *Attorney, Agent, or Firm* — Maier & Maier, PLLC

(57) ABSTRACT

Disclosed is a method for evaluating a physiological state depicting a person's resources, in which method the alternatives of physiological states depicting resources are determined, one or more contexts are selected, one or more variables are selected for each context, in which case in the evaluation the person's physiological information is measured and recorded, the measurement-background data of the measurement are determined and recorded, a value is defined for a variable of the context, corresponding temporal periods are defined for each context, and the person's physiological state is determined. Further, in the method a preselected correlation function is defined, a value is computed for the correlation function, a reference value is computed for each physiological state, and the physiological state of the person is determined. A corresponding system employing the method for evaluating a person's physiological cal state is also disclosed.

16 Claims, 10 Drawing Sheets

(51) Int. Cl.
  *A61B 5/024* (2006.01)
  *A61B 5/11* (2006.01)
(52) U.S. Cl.
  CPC .......... *A61B 5/1118* (2013.01); *G06F 19/345* (2013.01); *G06F 19/3481* (2013.01)

(56) References Cited

U.S. PATENT DOCUMENTS

| | | |
|---|---|---|
| 2004/0087839 A1 | 5/2004 | Raymond et al. |
| 2004/0152957 A1* | 8/2004 | Stivoric .................. A61B 5/01 600/300 |
| 2007/0173705 A1 | 7/2007 | Teller et al. |
| 2010/0286532 A1 | 11/2010 | Farringdon et al. |
| 2011/0004110 A1 | 1/2011 | Shusterman |
| 2011/0054290 A1 | 3/2011 | Derchak |
| 2011/0230732 A1 | 9/2011 | Edman et al. |

FOREIGN PATENT DOCUMENTS

| | | |
|---|---|---|
| WO | 2005/081168 | 9/2005 |
| WO | 2007/033194 | 3/2007 |
| WO | 2007/124271 | 11/2007 |
| WO | 2007/143535 | 12/2007 |

* cited by examiner

|  | State 1 | State 2 | State 3 | State 4 | State 5 | State 6 | State 7 | State 8 |
|---|---|---|---|---|---|---|---|---|
| Nighttime stress balance | | | | | | | | |
| Stressbalance 50 (Good) | 3 | 3 | 2 | 0 | -2 | -4 | -4 | 2 |
| Stressbalance 0 - 50 (Moderate) | (1) | 1 | 1 | 1 | 1 | -2 | -2 | 0 |
| Stressbalance <0 (Poor) (x) | -10 | -10 | -10 | 2 | 3 | 4 | 4 | -2 |
| Nighttime mean-value RMSSD | | | | | | | | |
| RMSSD >40 (Good) | 4 | 4 | 2 | -1 | 4 | -2 | -2 | -10 |
| RMSSD 20 - 40 (Moderate) | (3) | 3 | 1 | 1 | 3 | 0 | 0 | -10 |
| RMSSD 13 - 20 (Poor) (x) | -10 | -10 | -2 |  | -2 | 2 | 2 | -10 |
| RMSSD <13 (Pathological) | -20 | -20 | -10 | -10 | -10 | 2 | 2 | 6 |
| Time used for sleep | | | | | | | | |
| Sleep time > 7 h (Good) | (4) | 4 | -20 | 0 | 0 | 0 | 0 | 0 |
| Sleep time 5.5 - 7 h (Moderate) | 2 | 2 | 2 | 0 | 0 | 0 | 0 | 0 |
| Sleep time <5.5 h (Poor ) (x) | -2 | -2 | 2 | 0 | 0 | 0 | 0 | 0 |
| Recovery (state 6) in daytime | | | | | | | | |
| Good >60 min | 2 | -6 | 0 | -2 | -1 | -2 | -2 | 2 |
| Moderate 16 -60 min | (0) | -4 | 0 | 2 | 1 | 0 | 0 | 0 |
| Poor 0 - 15 min (x) | -2 | 2 | 0 | 1 | 1 | 2 | 2 | -2 |
| Nighttime RMSSD level higher than daytime (work-leisure vs. mean-value night) | (2) | 2 | 2 | 2 | 0 | 0 | 0 | 0 |
| How many daytime states identified as exercise | | | | | | | | |
| 0 - 2 h | (0) | 0 | 0 | 0 | 0 | 0 | -10 | 0 |
| 2 - 4 h | 0 | 0 | 0 | 0 | 0 | -2 | 4 | 0 |
| More than 4 h | -4 | -4 | -4 | -4 | -4 | -4 | 6 | 0 |
| Evaluation of loading risk | | | | | | | | |
| Recovery (state 6) in the time used for sleep | | | | | | | | |
| 75 - 100 % (Excellent) | (2) | 2 | 2 | 0 | -10 | -10 | -10 | 2 |
| 50 - 75 % (Good) | -2 | -2 | 2 | 4 | -4 | -10 | -2 | 2 |
| 25 - 50 % (Poor) | -10 | -10 | -2 | -2 | 2 | 2 | 2 | 0 |
| 0 - 25 % (Bad) | -20 | -20 | -10 | -10 | 2 | 4 | 2 | 0 |
| Recovery (state 6) one hour after going to bed | | | | | | | | |
| Good > 30 min | (2) | 2 | 1 | -10 | -1 | -4 | -4 | 1 |
| Moderate 5 - 30 min | 0 | 0 | 1 | -4 | 1 | -2 | -2 | 1 |
| Poor 0 - 5 min | -5 | -5 | -5 | 4 | 1 | 2 | 2 | -4 |
| Recovery (state 6) as % of day | | | | | | | | |
| > 30 % (Excellent) | 5 | 5 | -4 | 0 | -4 | -6 | -6 | 5 |
| > 25 % (Good) | (4) | 4 | -2 | 1 | -2 | -4 | -4 | 4 |
| 20 - 25 % (Moderate) | 2 | 2 | 1 | 1 | 1 | -2 | -2 | 2 |
| < 20 % (Poor) | -10 | -10 | 3 | 0 | 3 | 4 | 4 | -2 |
| Number of stress reactions during one day | | | | | | | | |
| Fewer than 50 % of day (Good) | (2) | 2 | 0 | 0 | -2 | -2 | 2 | 2 |
| 50 - 65 % (Moderate) | 1 | 1 | 0 | 0 | 1 | 2 | 2 | 1 |
| More than 65 % (Poor) | -10 | -4 | 0 | 0 | 0 | 4 | -2 | -2 |
| Resource vector return to at least initial level in measurement over one day. | (2) | 2 | 0 | 4 | -1 | -2 | 2 | 0 |
| Unidentified state in one day | | | | | | | | |
| 0 - 2 h (Few) | (0) | 0 | 0 | 0 | 0 | 0 | -4 | 0 |
| 2 - 6 h (Moderately) | 0 | 0 | 0 | 0 | 0 | 0 | 2 | 0 |
| > 6 h (Many) | 0 | 0 | 0 | 0 | 0 | 0 | 4 | 0 |
|  | | | | | | | | |
| Total state-identification points | 22 | 18 | -15 | 1 | -11 | -24 | -30 | -1 |
| Total maximum points | 28 | 28 | 14 | 20 | 15 | 22 | 30 | 20 |

Fig. 4a

| Preliminary-information form | | | | | | | | |
|---|---|---|---|---|---|---|---|---|
| Agree completely = 5 | | | | | | | | |
| Agree somewhat = 4 | | | | | | | | |
| Can't say = 3 | | | | | | | | |
| Disagree somewhat = 2 | | | | | | | | |
| Disagree completely = 1 | | | | | | | | |
| | | | | | | | | |
| 1. I think I take enough exercise for my health. Recommendation > 2 | | | | | | | | |
| 2. I think the effect of my exercise is enough to improve my fitness. Recommendation > 2 | | | | | | | | |
| | | | | | | | | |
| 3. I think my eating habits are healthy. Recommendation > 2 | | | | | | | | |
| | | | | | | | | |
| 4. I think I consume alcohol moderately. Recommendation > 2 | | | | | | | | |
| | > 2 | >2 | | | | | | |
| 5. I feel stressed. Recommendation > 4 | | | | | | | | |
| | <4 | <4 | <4 | >2 | >2 | >3 | >3 | >3 |
| 6. My day includes moments and breaks for recovery. Recommendation > 2 | | | | | | | | |
| | > 2 | <4 | >2 | >2 | >2 | <4 | <4 | <4 |
| 7. I often feel tired. Recommendation < 4 | | | | | | | | |
| | <4 | | | | | >2 | >2 | >3 |
| 8. I think I sleep enough. Recommendation > 2 | | | | | | | | |
| | >3 | >2 | <4 | <4 | <4 | <4 | <4 | <4 |
| 9. I feel I can affect matters relating to my own health. Recommendation > 2 | | | | | | | | |
| | | | | | | | | |
| 10. I have a sense of well being at the present moment. Recommendation > 3 | | | | | | | | |
| | | | | >2 | <4 | <3 | <3 | <3 |

Fig. 4b

|  | Reliability of interpretation | Feedback |
|---|---|---|
| Artefact information | | |
| Artefacts <10 % | 10 | |
| Artefact-% 10 - 20 % | 5 | |
| Artefacts > 20 % | -80 | Many measurement disturbances in material |
| Nighttime artefacts <10 % | 15 | |
| Nighttime artefact-% 10 - 20 % | 10 | |
| Nighttime artefacts > 20 % | -100 | Excessive measurement disturbances in material at night |
| Units of alcohol (Men/women) | | |
| 0 units (None) | 5 | |
| 1 - 2 units (Few) | 0 | |
| 3 - 6 / 3 - 4 units (Moderate) | -10 | Alcohol consumed moderately |
| 6 - 8 / 5 - 6 units (Many) | -20 | Much alcohol |
| >8 / >6 (Excessive) | -40 | Excessive alcohol |
| Identification points | | |
| <0 % (Insufficient) | -100 | State identification has not found a suitable state |
| 0 - 40 % (Poor) | -40 | State identification has found only few properties corresponding to a state |
| 40 - 60 % (Border-line case) | 5 | |
| 60 - 80 % (Moderate) | 30 | |
| 80 - 100 % (Good) | 50 | |
| Length of material | | |
| 0 - 15 h (Insufficient) | -100 | Not enough material |
| 15 - 20 h (Poor) | -40 | Barely sufficient material |
| 20 - 22 h (Moderate) | 5 | |
| 22 - 26 h (Good) | 20 | |
| 26 - 28 h (Moderate) | 5 | |
| > 28 h (Excessive) | -40 | Excessive material, material should correspond to about one day (24 h) |
| Illnesses | | |
| Temporary illness -100 % - 0 % | 0 | |
| Medications | | |
| Total | 30 | |

Fig. 5

| State | 1 | 2 | 3 | 4 | 5 | 6 | 7 | 8 |
|---|---|---|---|---|---|---|---|---|
| | 100 | 100 | 10 | 10 | 0 | 0 | 0 | 10 |
| | 80 | 100 | 10 | 10 | 0 | 0 | 0 | 0 |
| | 75 | 95 | 5 | 5 | 0 | 0 | 0 | 0 |
| | 100 | 80 | 55 | 10 | 0 | 0 | 0 | 10 |
| | 80 | 55 | 55 | 10 | 10 | 0 | 0 | 0 |
| | 95 | 75 | 50 | 5 | 0 | 0 | 0 | 5 |
| | 100 | 80 | 10 | 10 | 0 | 0 | 0 | 10 |
| | 0 | 0 | 10 | 0 | 55 | 55 | 0 | 0 |
| | 0 | 0 | 10 | 10 | 80 | 55 | 0 | 0 |
| | 75 | 50 | 50 | 5 | 5 | 0 | 0 | 5 |
| | 10 | 10 | 10 | 55 | 10 | 0 | 0 | 0 |
| | 100 | 80 | 10 | 55 | 0 | 0 | 0 | 10 |
| | 40 | 20 | 0 | 0 | 0 | 0 | 0 | 0 |
| | 75 | 75 | 5 | 50 | 0 | 0 | 0 | 0 |
| | 0 | 0 | 0 | 0 | 0 | 0 | 0 | 0 |
| | 0 | 0 | 10 | 10 | 80 | 80 | 0 | 0 |
| | 100 | 80 | 10 | 10 | 0 | 0 | 0 | 10 |
| | 10 | 10 | 10 | 0 | 55 | 10 | 0 | 0 |
| | 10 | 0 | 10 | 0 | 0 | 0 | 0 | 0 |
| | 95 | 75 | 50 | 5 | 0 | 0 | 0 | 5 |

Fig. 6

BACKGROUND INFORMATION 143

Edward Example

| | |
|---|---|
| Age (years) | 26 |
| Height (cm) | 177 |
| Weight (kg) | 72 |
| Rest heart rate (beats/min) | 40 |
| Max. heart rate (beats/min) | 194 |
| Weight index (BMI) | 23 |
| Activity class | 7.0 |

Contact information
| | |
|---|---|
| Address row 1 | Koivutie 2 |
| Address row 2 | - |
| Address row 3 | - |
| Post code | 40100 |
| City | Jyväskylä |
| Country | Finland |
| Email | edward.example@sposti.fi |
| Tel. | +358 535266446 |
| Organization | |

Long-term illnesses and medication:
-

Automatic state identification and additional information 144

Automatic state identification and additional information:

| | Alcohol | Medication |
|---|---|---|
| Day 1: 20 March 2011 | | Common-cold |
| Day 2: 21 March 2011 | 2 units | antibiotic |
| Day 3: 22 March 2011 | | |
| Summary | 2 units | |

| Sleep quality | Identified state | Reliability of information |
|---|---|---|
| GREEN | Delayed recovery | Poor |
| YELLOW (4) | Temporary overload | Moderate |
| RED (6) | Delayed recovery | Good |
| YELLOW (4) | Temporary overload | Moderate |

— 140  — 141  — 142

The purpose of automatic state identification is to condense the information obtained from multi-dimensional heart rate measurements into a form more easily interpreted to an expert. On the basis of the measurements in the period, a summary is created, which depicts the totality of the measurement-period result, e.g. a period of three days. The automatic state identification is not intended to reduce the role of the expert in providing feedback, but to act as an effective tool in familiarization with the results.

146

GREEN, GREEN-YELLOW, YELLOW-GREEN, YELLOW, ORANGE, RED, BLUE, GREY, WHITE

1. Good recovery
2. Good recovery, but lacking daytime recovery
3. Moderate recovery, but night sleep short
4. Delayed recovery
5. Temporary overload
6. Extended stress or overload
7. Physical overload
8. Burnout / physiologically deviant state
9. Unidentified

Notes 145

To be taken into account in evaluation:
-

Provider:   This report has been produced by Well-Being Analysis (v 5.0.0.98)   Analyser:

Fig. 7

| Questions: | Replies: | | | | |
|---|---|---|---|---|---|
| | Disagree completely | Disagree somewhat | I can't say | Agree Somewhat | Agree completely |
| 1. I think I take enough exercise for my health. | 1 | 2 | 3 | ④ | 5 |
| 2. I think the effect of my exercise is enough to improve my fitness. | 1 | 2 | ③ | 4 | 5 |
| 3. I think I my eating habits are eat healthy. | 1 | 2 | 3 | ④ | 5 |
| 4. I think I consume alcohol moderately. | 1 | 2 | ③ | 4 | 5 |
| 5. I feel stressed. | 1 | ② | 3 | 4 | 5 |
| 6. My day includes moments and Breaks for recovery. | 1 | 2 | 3 | ④ | 5 |
| 7 I often feel tired. | 1 | 2 | ③ | 4 | 5 |
| 8. I think I sleep enough. | 1 | 2 | 3 | ④ | 5 |
| 9. I feel I can affect matters relating to my own health. | 1 | ② | 3 | 4 | 5 |
| 10. I have a sense of well being at the present moment. | 1 | 2 | 3 | ④ | 5 |

Fig. 8

METHOD AND SYSTEM FOR EVALUATING A PHYSIOLOGICAL STATE DEPICTING A PERSON'S RESOURCES

TECHNICAL FIELD

The present invention relates to a method for evaluating a physiological state depicting a person's resources, in which method the alternatives of physiological states depicting resources are determined, one or more contexts are selected, each corresponding to a temporal period for the activity/state of the person, one or more variables are selected for each context, when, in the evaluation the person's physiological data are measured and recorded as a continuous measurement for at least 4 h, preferably for 50-80 h, containing one or more selected context, the measurement-background data of the measurement are determined and recorded, with the aid of the recorded measurement, a value is defined for each selected variable of the context, from at least one corresponding defined period, corresponding temporal periods are defined for each context, and the person's physiological state is determined exploiting the measurement-background data, using the preselected criteria and the measured value of the variable of each context.

The invention also relates to a corresponding system for determining the physiological state of a person.

BACKGROUND OF THE INVENTION

Lifestyle-related diseases are one of the greatest threats in modern society. The most widespread diseases include obesity, high blood pressure, diabetes, detrimental cholesterol and blood-fat values, as well as diseases of the cardiovascular system. They are often related to the wrong kind of food, insufficient exercise, insufficient or poor sleep, as well as stress and ultimately burnout. The problems can also often be related to social problems, excessive use of alcohol, and marginalization.

The problem is worldwide and the degree of development of a problem often depends on the degree of development of the society. As the overall welfare of a society increases, problems deriving from it are often encountered. In healthcare systems, resources are frequently only sufficient to care for the consequences of problems and not to prevent them. General education relating to lifestyles helps up to a certain point, but individuals often find it difficult to recognise their own problems, never mind solve them.

One way to prevent problems is to monitor a person's physiological signals, on the basis of which conclusions can be drawn on the person's physiological state at the time. The physiological signals from a person's body are often quite difficult to interpret and the interpretation depends on a great deal of other information, such as personal background data (age, height, weight, sex, fitness level, exercise activity), illnesses and their associated medicines, or related context information, such as whether the person is sleeping or awake, at leisure or at work. Together, all of these factors form a highly complex decision surface, which is difficult to manage and the understanding of which demands broad and long training. The interpretation easily becomes dependent on the person involved and subjective, which naturally exposes it to errors and feedback of uneven quality.

In other words, an individual physiological parameter with no context information is very open to interpretation, but if, for example, the same person's heart rate variations while sleeping and during the day or during work and during leisure are known and can be compared, this will already make it considerably easier to determine the person's physiological state. Automatic interpretation of the physiological state combined with measured bio-signals will provide an effective tool for lifestyle counseling.

Earlier methods have typically attempted to standardize the context. This means that a simple test situation is created, in which an attempt has been made to minimize all the other active factors. This, however, loses an important link to real life related to lifestyle counseling, as it is precisely the factors that are standardized to which attention should be paid in lifestyle. Such tests are, for example, investigating the orthostatic heart rate reaction and other tests on the operation of the autonomic nervous system. It has a considerably greater effect to give feedback from an individual's daily life, when real changes in everyday life can also be suggested to the individual. Changes in everyday life are the key to permanent changes in lifestyle. Previous methods aiming at the automation of interpretation are also largely medical programs for creating a diagnosis and cannot be utilized in determining everyday well-being.

In publication U.S. Pat. No. 5,755,671, Albrecht et al. have used frequency bands in heart rate variation when estimating a person's risk of developing cardiovascular diseases. The program compares the heart rate variation frequency bands with predefined values and creates an interpretation on this basis. However, in the method in question only a single variable is used, along with the related reference values, so that it is a very simple method. The interpretation of a single variation without context information does not provide very much information on a person's well-being in normal life.

Sriram et al. in publication WO 2005081168 and Mazar et al. in publication WO 2004047624 have also disclosed a method aimed at automating interpretation which are based on earlier interpretations made by an expert. The computer-aided diagnosis of Sriram et al. is intended to act as support for expert decision making when determining cardiac diseases. The interpretation is based on the patient's data and on an ultrasound image of the heart, so that the analysis is very narrow and is useful only when investigating the state of the patient's heart. For its part, the method of Mazar et al. uses more extensive databases as a base for its interpretation, with the aid of which the patient's health can be determined automatically. The program runs in a web environment and is a so-called remote physician, but is limited to clinical use. In their solution, Mazar et al. do not, however, explain how the person's health is interpreted by combining data from databases and measurement data.

The method disclosed by Hadley in publication WO 2007124271, which concentrates on determining the risk of death due to cardiac failure by monitoring recovery from exercise, also relates to a similar detection of state. The method is connected integrally to a fitness test and to determining heart rate level during loading and recovery. Thus the method cannot be utilized to determine the degree of loading of events in daily life and the analysis it provides is indeed limited very narrowly to the monitoring of heart rate level and on this basis to determining recovery.

In publication U.S. Pat. No. 7,330,752, Kettunen et al. disclose a system for segmenting and analysing an ambulatory heartbeat interval signal, in order to detect a stress state. In the system, it is not possible to interpret or classify whether the detected physiological state is positive or negative in terms of a person's health.

Publication WO 2007/143535 A2, which discloses a device and method for detecting sleep apnea, is also known from the prior art. In the method, three variables are measured and their values are classified as belonging to a specific state depicting sleep quality. However, the classification becomes extremely cumbersome if there is an increase in the number of variables and states depicting sleep quality.

SUMMARY OF THE INVENTION

The invention is intended to create a better method than those of the prior art for evaluating a physiological state depicting a person's resources. With the aid of the method, it is possible to comprehensively and reliably determine nighttime and daytime stress and recovery, from the effects of exercise to the quality of sleep. The characteristic features of the present invention are stated in the accompanying claim 1. The invention is also intended to create a better system than those of the prior art for determining the physiological state of a person. The characteristic features of the system according to the present invention are stated in the accompanying claim 16.

The intention of the method according to the invention can be achieved by means of a method for evaluating a physiological state depicting a person's resources, in which method alternative physiological states depicting resources are determined, one or more context is selected, each corresponding to the temporal period of a selected measurement, one or more variables is selected for each context, and a preselected correlation function is defined for each variable in each physiological state. In the evaluation, the person's physiological data are then measured and recorded as a continuous measurement for at least 4 h, preferably for 50-80 h, containing one or more selected context, and the person's background data from the time of the said measurement are collected and recorded. Further, the temporal periods corresponding to each context are determined with the aid of the background data and a value for each preselected correlation function is computed using the values of the variables and the time period of the corresponding function. Finally, with the aid of a preselected sum function, a reference value for each physiological state is computed by combining the values of all the calculated functions of each physiological state and determining the physiological state of the person from the reference values by using a preselected criterion.

By means of the method according to the invention, measurement information, initial data provided by the person, and the person's subjective estimate of their own state can be combined into a single totality, which finally provides an easily interpreted and understood result. The result is easy to present to the person being examined and service provider performing the method on the person can concentrate on the reasons for the person's problems or the prevention of such problems.

The context is preferably one or more of the following: night, day, sleep time, exercise, recovery, work, leisure. The contexts are periods of time during the person's measurement period, which contain some function telling the state of health, such as exercise or sleep. When the measurement information is interpreted in the light of the context information, a good estimate can be achieved of the physiological state of the person being examined.

In the method, 1-15, preferably 2-10 contexts can be selected. A comprehensive result is achieved by using a sufficient number of contexts.

According to one embodiment, in the method a person's physiological data are measured and recorded as a continuous measurement over a specific period of time, which period of time is arranged to be such that at least one context is detected on the basis of the measured physiological data. Thus measurement and personal background data are not necessarily required at all.

The variables of the context are preferably one or more of the following: nighttime stress balance, daytime stress balance, night RMSSD, day RMSSD, time used for sleep, recovery for work and leisure, night RMSSD relative to day RMSSD, daily exercise, recovery from sleep time, time from the start of recovery when going to sleep, daily recovery, daily number of stress reactions, daily undetected state, recovery of resource profile. The context variables are linked to the manner of performing the measurement, i.e. whether, for example, the heart rate or movement of the person being examined is measured.

According to one embodiment, the preselected correlation function is a step function. Thus the individual function easily receives discrete values, which are easy to process.

According to one embodiment, at least one or more of the following: age sex, height, weight, activity class, are used additionally in the method as personal background data. The background data greatly influence the interpretation of the measurements.

On the basis of the measurement data and the measurement background data and/or the personal background data, a reliability coefficient is preferably defined. The reliability coefficient helps the service provider to estimate the correctness of the defined physiological state.

The measurement background data are preferably collected from the person's subjective estimate of the person's physiological state, which subjective estimate, the reliability coefficient, and the physiological state determined on the basis of measurement are compared to each other, to allow feedback and counseling to be given to the person. The evaluation of the physiological state is performed in order to measure the well-being of the person being examined and on its basis the service provider counsels the person towards a healthier lifestyle. The method makes the interpretation of the measurement data and the possible subjective estimate considerably easier than in methods according to the prior art, so that the service provider requires less work and competence when interpreting the results. In the comparison, contradictions are sought between the background data and the features of the defined physiological state. For example, if the person being examined feels that they are stressed, but the defined state suggests moderate recovery, this information can be utilized in the service provider's analysis.

6-20, preferably 8-10 physiological states can be defined. By means of the definition of physiological states it is sought to form a clearer picture of the current well-being of the person being examined and in part also to motivate them to move to an even better state.

The physiological state of the person is preferably determined by comparing a reference value of each state with the maximum value of the sum function of the values of the preselected correlation functions. Thus, the reference value of the physiological state, which is closest to the sum function of the relevant state, can be interpreted as being the physiological state of the person in question.

The physiological data of the person are preferably measured and recorded in the person's normal living circumstances. The term normal living circumstances refers to the person's normal everyday routines, i.e. the person lives normally during the measurement. Measurements are not performed in special measurement conditions, which differ from the person's normal life situations.

The person's physiological data are preferably measured with the aid of heart rate measurement. Several different variables can be distinguished in the heat-rate data, which correlate with the person's physiological state.

According to a second embodiment, the method is used in PC software.

According to a third embodiment, the method is used in an ECG/pulse-measurement device.

1-10, preferably 1-5 context variables are preferably selected. A sufficient number of variables improves the method's reliability.

According to one embodiment, in the method the person's physiological data are measured and recorded as a continuous long-term measurement for at least one week, preferably for several weeks, and even for 100 days. The personal and measurement-background data can be determined from long-term measurement directly from the measured physiological data by means of separation of the parameters.

The intention of the system according to the invention can be achieved by arranged by means of a system for evaluating a physiological state depicting a person's resources, in which system the person's physiological state is determined on the basis of a measured physiological state, which system includes a mobile measurement device for measuring the person's data as a continuous measurement, which mobile measurement device further comprises means for recording the said data. The system also includes software means for determining the physiological state, a computer for the user of the system, comprising a user interface for entering the initial parameters to the software means, and means for collecting the person's background data, comprising a second user interface. The system further includes a data-transfer network and a server for transferring the person's background data to the computer. The software means belonging to the computer comprise a preselected correlation function for each variable in each physiological state for calculating a correlation value using the values of the variables, a preselected sum for calculation a reference value for each physiological state by combining the correlation values of all the correlation functions of all the physiological state, in order to determine the reference values using a preselected criterion. The system automatically interprets the physiological state measured from the person being examined, on the basis of empirical information, which saves the user a considerable amount of time.

With the aid of the automatic method interpreting bio-signals and context information relating to bio-signals, to which the invention relates, individual feedback relating to lifestyle can be provided cost-effectively.

The invention reduces the amount and extent of training required to interpret a physiological state, accelerates the creation of feedback, as well as improves the quality of the feedback by increasing objectivity and reducing erroneous interpretations. In addition, the service provider can also concentrate to a greater extent on means of developing the customer's lifestyle, instead of interpreting what the person's measured data tell about them. Automatic state detection allows the expert to concentrate on providing feedback. Together all these factors improve the experience gained from the service and also permit health care to concentrate more on prevention instead of caring for illness.

The invention relates to a system for automatically interpreting bio-signals and the related context information. With the aid of the invention, feedback relating to lifestyle can be provided cost-effectively, on the basis of which a person can be counseled towards a healthier and more productive life. In a preferred embodiment, the invention relates to the combination of heartbeat interval parameters calculated from one or more days' heartbeat interval measurement and the related context information (e.g., during sleep, while awake, at work, during leisure), to form ready interpreted feedback. The feedback defines the person's physiological state unambiguously, for example, using the following scale:
1. 'Good recovery'.
2. 'Good recovery, but daytime recovery is lacking'.
3. 'Moderate recovery, but nighttime sleep was short'.
4. 'Delayed night recovery'.
5. 'Poor recovery'.
6. 'Overload'.
7. 'Physical overload'.
8. 'Burnout state/physiologically deviant state'.

In the invention, dispersed data are collected and combined, for example parameters calculated from heartbeat intervals with context information and personal individual background data, to be able to detect a physiological state.

In this connection, the term physiological state refers to a state determined through physiological measurement, which depicts the person's mental and physical resources available during the measurement period.

BRIEF DESCRIPTION OF THE DRAWINGS

In the following, the invention is described in detail with reference to the accompanying drawings depicting some embodiments of the invention, in which FIG. 4a shows a practical example of the state matrix used in the method according to the invention, FIG. 4b shows a practical example of the preliminary-information portion of the state matrix used in the method according to the invention, FIG. 5 shows the reliability table used in the method according to the invention, FIG. 6 shows the correlations of different states relative to each other, in the method according to the invention, FIG. 7 shows the results form used in the method according to the invention, FIG. 8 shows the preliminary-information form used in the method according to the invention.

DETAILED DESCRIPTION OF THE INVENTION

Figure 1:
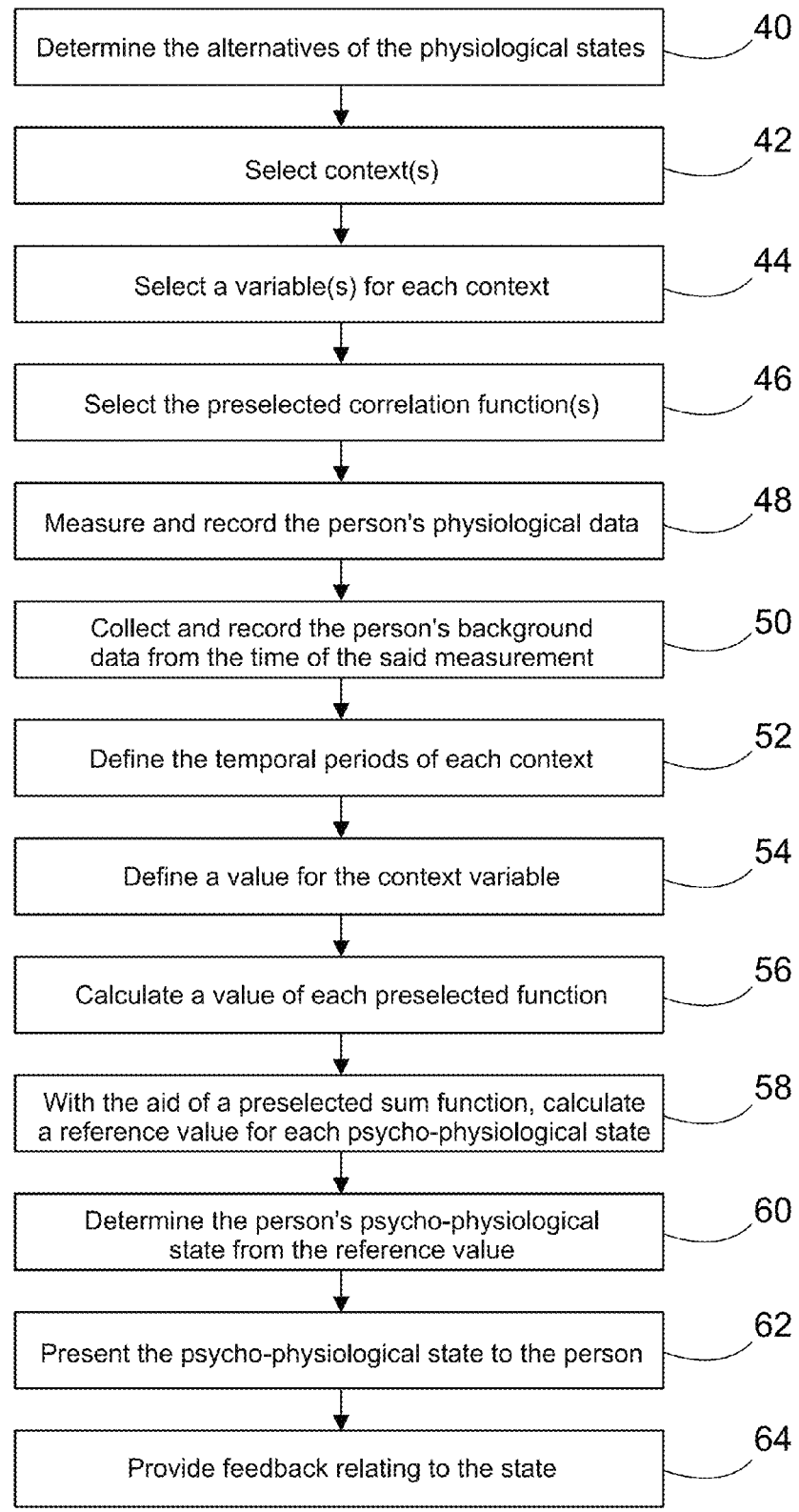
FIG. 1 shows a flow diagram of the stages of the method according to the invention.

FIG. 1 shows the stages 40-62 of the method according to the invention. The method is used to evaluate the physiological state of the person being examined. In this connection, the term physiological state refers to a long-term state of being predominating in the person being examined, over at least the period of the measurement. Psychological factors too can affect the physiological state. The method can be used by, for example, a well-being services provider, who evaluates the state of a person being examined, provides feedback and counseling and, if necessary, prescribes medicine or therapy for the problems of the person being examined. In principle, the method is even suitable for use by a person completely unacquainted with health care, as the result of the method is in a clearly understandable form. The service provider's employee presenting the result of the method to the person being examined is preferably, for example, a nurse, a doctor, a psychologist, or similar healthcare professional, who can give counseling and assistance with possible problems.

The method is preferably implemented with the aid of software means, for example, as a computer application.

In the method, the person's physiological state is evaluated. The service provider, i.e. the user of the method, can freely define the physiological states in stage 40. The various states can be, for example, eight and they can be, for example: 'Good recovery', 'Good recovery, but daytime recovery is lacking', 'Moderate recovery, but night-time sleep was short', 'Delayed night recovery', 'Poor recovery', 'Overload', 'Physical overload' or 'Burnout state/physiologically deviant state'. It should be noted that although separate classes are described here, the physiological state can also be defined as a sliding state, so that it can be situated at a point between two classes, or be a probability for specific states.

In stage 42, the service provider defines for the method one or more contexts, each corresponding to a temporal period for the activity/state of the person. 1-15, preferably 2-10 contexts can be selected. A context is a period of time, which can be, for example, night, day, sleep time, leisure, night relative to day, working time, or some other corresponding period of time. A context can also be a longer period of time, for example, a weekend, a holiday, or some rhythmic life event, such as travelling, or going shopping. The context is selected in such a way that the period of time depicts some daily function of the person being examined, for example, exercise or sleeping. Contexts are characterized by the fact that they contain some specific individual function, but an individual context can also include several functions. The entire measurement period is preferably able to be divided into different contexts, all of which for their own part depict the physiological state of the person being examined.

In stage 44, after defining the context or contexts, one or more variables are defined for each context. The variables can be, for example, night stress balance, mean RMSSD, recovery, or exercise share. There can also be other context variables, of which context variables 1-10, preferably 1-5 are selected. Sufficient reliability for the defined physiological state can be achieved by using sufficiently many context variables. Each variable is characterized by being able to be monitored by using the measurement used in the method. The measurement can be one depicting any physiological state whatever of the person being examined, for example, the person's movement or heart rate. Different measurements can be used to monitor different variables.

After this, in stage 46 a preselected correlation function is defined to depict the relationship between each physiological state and the variables defined for each context. The preselected correlation functions are formed by physiological experts on the basis of empirical information, by means of which the value of a variable of a specific context is weighted for a specific physiological state. The value of the correlation function depicts how well the value of the variable of the context correlates with the relevant physiological state. In other words, the correlation functions are preferably formed from a large quantity of physiological information based on empirical information.

The two aforementioned selections can be made in the program for the method, by which the method is implemented. Through the selections, it is possible to influence considerably the comprehensiveness of the result obtained by the method and the feedback received from the method. When selecting more contexts, more measurement data will be obtained and through this information on the physiological state of the person being examined.

After this, in stage 48 the person's physiological state or other state depicting their activity is measured and recorded, for example, movement using a motion sensor, as a continuous or partly continuous measurement for at least 4 h and preferably 50-80 h, containing one or more selected contexts. The physiological information can also be recorded entirely or in part indirectly, for example with the aid of acceleration measurement. The method can also be implemented without heart rate measurement, by measuring the physiological state indirectly or directly using, for example, positioning (GPS/GNNS), a camera, EMG, or temperature. Information on the person's activity, reported by the user or automatically detected, from the period of the measurement is collected and recorded, in order to distinguish different contexts. The measurement is preferably performed when the person is performing normal everyday routines.

According to one embodiment, the method can also be used by continuing the measurement for at least one week, preferably for several weeks, even for 100 days, in which case measurement or personal-background data may not necessarily be needed at all. During such long measurement periods, the necessary background information can be deduced from the measured physiological information. In a measurement over even one week, the rest heart rate can be deduced from the measured physiological information, which can then be used to detect rest. Over longer measurement periods, the person's fitness level (VO2max or METmax) and their maximum heart rate (maxHR) can be determined. In longer measurements, GPS or other positioning is preferably additionally used in the method, so that, for example the person's running speed can be obtained from jogging runs and through it the fitness level can be determined reliably. The rest heart rate can generally be determined from much shorter measurements of, for example 1-3 days, especially if the measurement includes night/sleep time when the person is asleep, when the heart rate is usually at its lowest. The collected and recorded data can be, for example, heart rate data collected using a heart rate monitor or pulse oximeter (pulse pletysmogram, based on measuring the pulse waves caused by heartbeats detected in the blood flow using the photodiode method), motion data collected by an acceleration sensor, or other similar information, which can be recorded in the memory of the relevant device, or over a remote link to the memory medium in the same device using the software used in the method.

In addition, according to stage 50, measurement data 22 from the measurement from the measurement period in question are preferably determined and recorded from the person being examined. Data that are detected or notified by the user can be, for example, the times of going to sleep and waking up, in order to determine the duration of sleep. The measurement background data can be, for example, activities performed during the measurement period, in a diary form. Besides measurement background data 22, in the method personal background data 23 can be determined and recorded. Both personal and measurement background data can be collected as a questionnaire, which can take place by filling a preliminary-information form on paper, directly to the measuring device, or over a web link. Measurement background data can preferably be determined automatically, for example by acceleration measurement, GPS positioning, or similar measurement.

Figure 2:
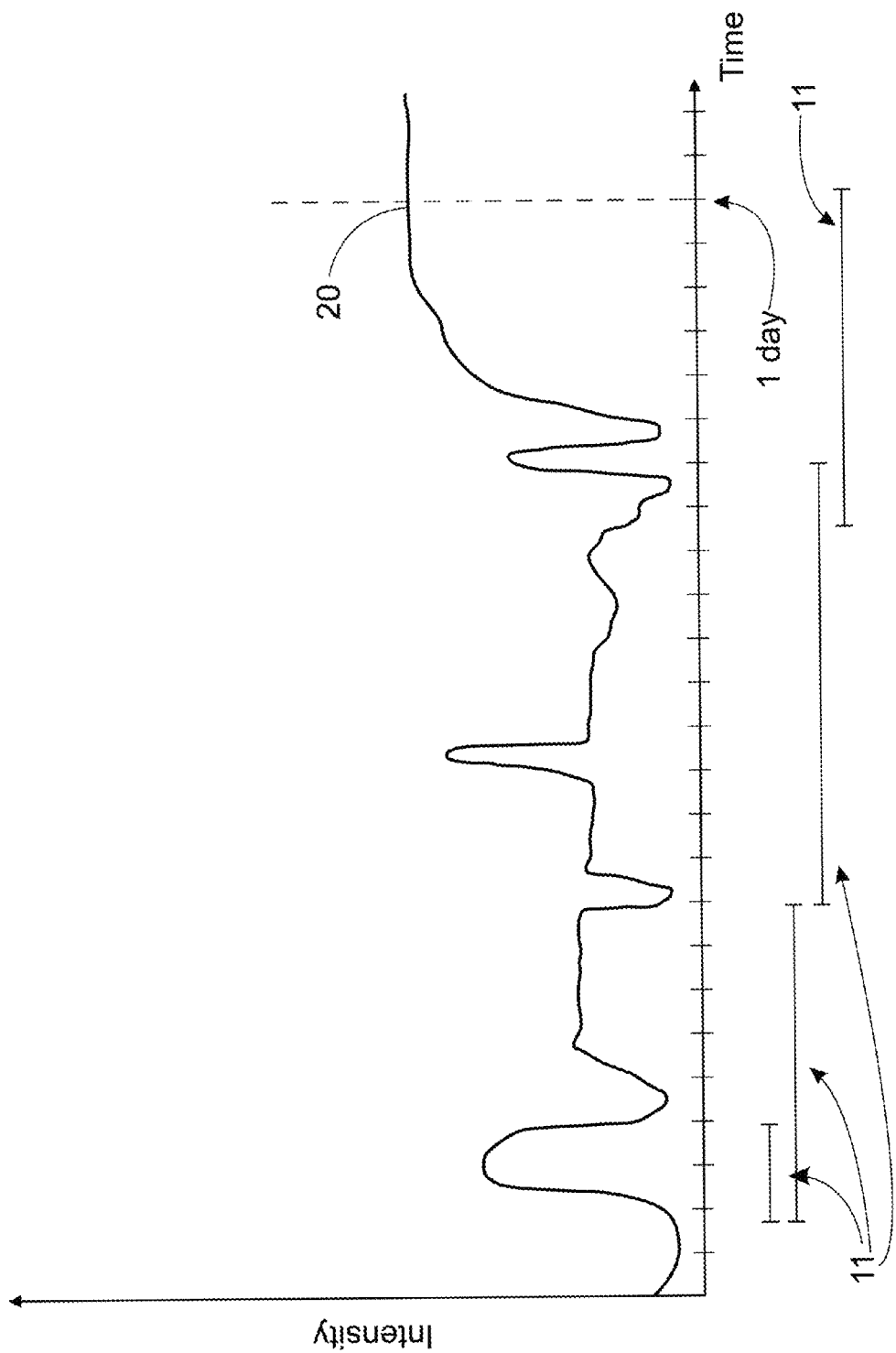
FIG. 2 shows the method according to the invention's definition of a context from measurement data.

Temporal periods corresponding to each context can be defined on the basis of the measurement data and background data, by means of software or manually, in stage 52 of FIG. 1, according to FIG. 2. Definition by means of software can be automatic, in which, for example, the fact that the person is asleep can be deduced from heart rate data or from data measured using a motion sensor. Alternatively, the user of the method, for example a service provider, can define manually the temporal periods corresponding to the contexts in the program. Measurement-background data is preferably used to define the contexts. In FIG. 2, the measured physiological information 20 has been the heart rate variation of the person being examined, which is shown as a curve 20. The areas of highest intensity, the areas of lowest intensity, and various shapes can be found from the shapes of the curve 20. On the basis of the differences between the areas, it is possible to distinguish different contexts 11, which preferably form a continuity. The contexts can be partly or entirely overlapping, consecutive, or there can be discontinuities between them, in which case no context appears in the area in question. With the aid of the recorded measurement data, a value is defined for a variable of each selected context, from a period defined for a specific context. The variable value of the selected context can be, for example, the value of the stress balance, recovery of RMSSD, or share of exercise.

Next, in stage 54 a value is calculated for each of the preselected correlation functions using the value of the said variables. According to FIGS. 3-4*b*, for example, in the case of the variable 12 'time used for sleep' C of the context 11 'sleep time', the preselected correlation function for the physiological state 10 '1—good recovery' receives the values 14, which can be, for example −2, 2, or 4, depending on how much the person being examined has been asleep, i.e. how great the value 26 of the variable has been. The preselected correlation functions are preferably step functions, so that, for example, with the value 7.0 h of the context variable the correlation function receives the value 2, but immediately with the value 7.1 h the correlation function receives the value 4. In practice, the value of each correlation function depicts how well the value of the variable depicts precisely the relevant physiological state. For example, when the context variable 'time used for sleep' receives the value 4, it can be ascertained that such a time used for sleep depicts poorly the state 'good recovery', in which case the value of the correlation function will be negative. On the other hand, the variable value 8 h depicts well the state 'good recovery', in which case the correlation function will receive the Positive value 4.

In stage 56, a value of the variable and a correlation coefficient depicting the correspondence to the physiological state are computed for each physiological state with the aid of a correlation function using each value of the variable. For example, in the context 'nighttime' for the value 51 of the context variable 'stress balance', the preselected correlation function of each state receives a value, in this case from state 1 to state 8: 3, 3, 2, 0, −2, −4, −4, and 2, as a function of eight physiological states. The preselected correlation function of state 1 receives the value 3, because the stress balance value 51 depicts well the state 1 'good recovery'. On the other hand, the preselected function of the state 6 receives the value −4, because the stress balance value 51 depicts poorly the state 6 'overloaded'. It should be noted that the correlation functions can also be continuous, when the variable values will not be classified in the classes, for example, good, moderate, and poor. The table in FIG. 4*a* shows examples of the values of the correlation functions. If the correlation function receives the value 0, it means that the context variable in question in no way depicts the relevant physiological state. In FIG. 4*a*, the values received by the correlation functions of the variables a show as an example a circle around the physiological state 1. Based on the circled values, the result here is a reference value of 20 in the case of state 1.

Once the program has calculated a preselected correlation function 24 (shown in FIG. 6) for each variable 12 of the context 11 on the basis of the value 14 for each physiological state 10, the preselected sum function 27 (shown in FIG. 6) can be used in the calculation, in stage 58, of a reference value 16 for each physiological state, by combining all the values of the correlation functions calculated for each physiological state. The calculated reference values can be, for example, the values shown in the columns in the table of FIG. 4*a*.

Finally, the physiological state of the person being examined is determined in stage 60 from the reference values by using the preselected criteria. For example, the state that has received the most points relative to the maximum points for the state in question can be chosen as the physiological state. In other words, the sum function value 16 of each physiological state is compared to the value 18 of the sum function of the maximum values of the correlation functions 24 of each physiological state.

The aforementioned stages are not necessary in a binding sequence. For example, the variables can be selected after the measurement of the physiological data, as the values of the variables can be identified from the measurement data that has already been entered.

The automation of the interpretation is intended to summarize the multi-dimensional information, for example on daily measurements of heartbeat interval, into a more easily interpreted form. The method requires, for example, material containing heartbeat interval measurements from one or more days. Person background data 23, which can be, for example, the following: age, sex, height, weight, activity class; optionally maxHR (maximum heart rate, minHR (rest heart rate), maxVO2 (maximum oxygen consumption, i.e. fitness level), are preferably determined and recorded for the method. The method can also be implemented without the collection of personal background data, so that, for example, the personal background data required in long-term measurements (for example, rest heart rate) are obtained automatically from the measurement data. In addition, the method preferably requires the person the fill a preliminary-information form/questionnaire to evaluate the person's physiological state, i.e. their subjective evaluation of their own physiological state. In terms of the method, it is also important to know the number of units of alcohol consumed during the measurement period, because the consumption of alcohol greatly affects the quality of sleep, heart rate variation, heart rate level, and the variables calculated from these. All the aforementioned data are the method's background data.

The result produced for the person by the method includes the state analysed from the daily measurement according to stage 62, the reliability of the state detection and interpretation, as well as suggests for measures relating to the detected state. In addition, a mean-value state for several consecutive days can be produced, which gives the best depiction of the entire measurement period (for example, three days), allowing the interpretation and the feedback given to the customer in stage 64 to be further simplified. Further, the states can be defined hierarchically as 'good-bad', which will make long-term monitoring, for example, both possible and reasonable.

Figure 3:
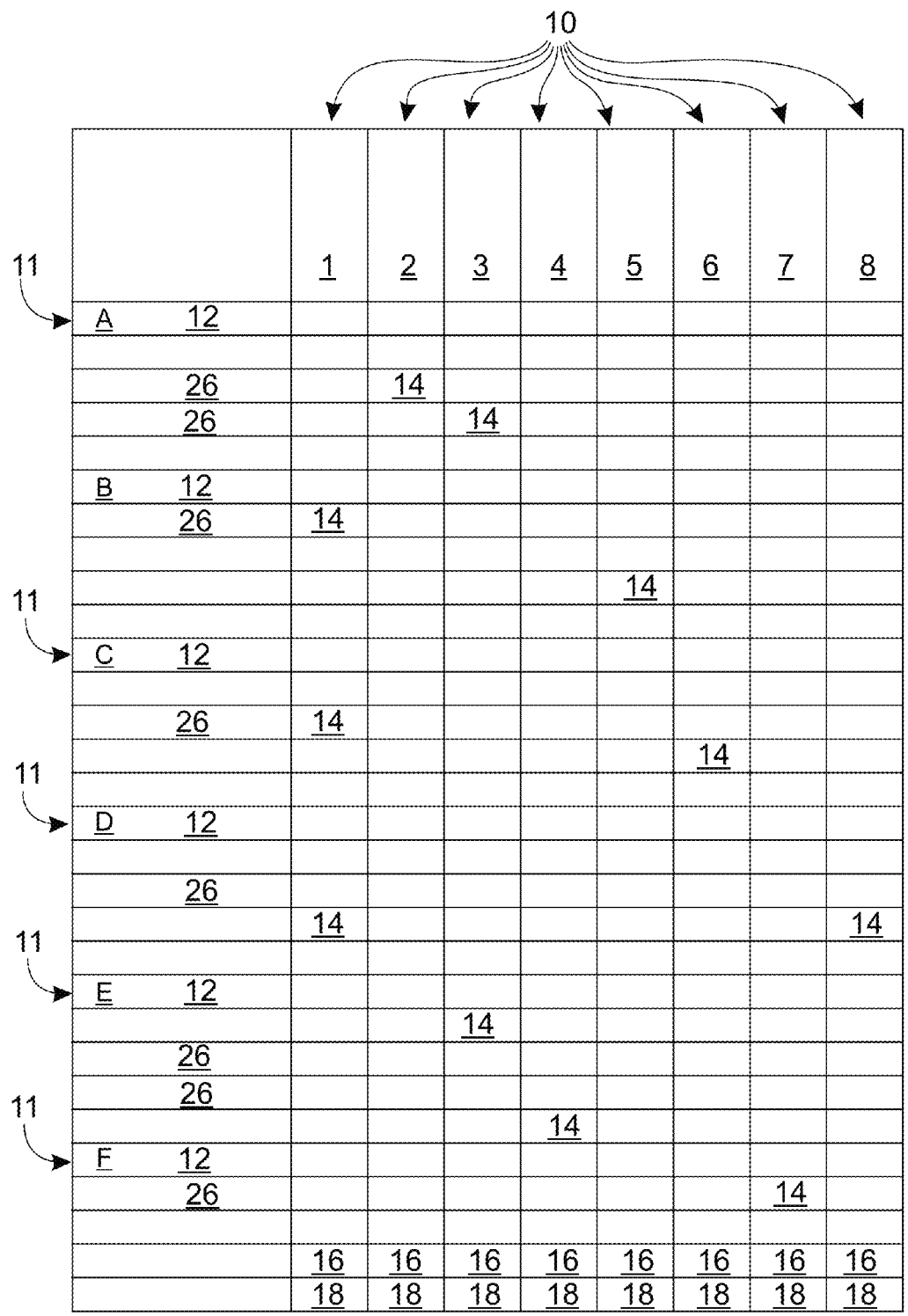
FIG. 3 shows a simplified example of the state matrix used in the method according to the invention.

The calculation in the method can be depicted by means of the state matrix according to FIGS. 3-4b, which combines the physiological data measured from the person with expert data. The following describes the variables that can be calculated in the evaluation for different contexts.

A) Night Stress Balance

Night stress balance is based on the detection of stress and recovery states, which is disclosed in, for example, publications EP1545309 and U.S. Pat. No. 7,330,752. The heartbeat interval signal can be segmented for the stress balance, so that the stress and recovery states will be brought out more clearly. The stress balance is simply the relation between the temporal durations of the stress and recovery states. The night stress balance tells what the relation is at night between the temporal duration of detected stress and recovery. The night stress balance can be classified, for example in the classes >50 (good), 0-50 (moderate), and <0 (poor). When the stress balance is >50 (good), most of the sleep time is used for recovery and the body recovers well. When the stress balance is 0-50 (moderate) the body's recovery is somewhat delayed, but nevertheless there is more recovery relative to stress reactions. Further, when the stress balance is <0 (poor) recovery is less than stress reactions during the night. The body is running at an excessive rate and, among other things, the heart rate does not return effectively from daytime stress. This stress balance class shows clearly that recovery has slowed.

B) Night RMSSD

Night RMSSD is a generally used mathematical numerical value depicting the amount of heart rate variation, calculated from signals, which is linked to the level of activity of the parasympathetic branch of the human autonomic nervous system. Heart rate variation (RMSSD) depicts the regulation of the autonomic nervous system. A high heart rate variation is linked with recovery, rest, and welfare. A low heart rate variation that appears without physical stress tells for its part of deficiency or abnormal regulation in the autonomic nervous system and can indicate, among other things, stress reactions, long-term loading, or certain diseases. At rest, the heart rate should drop and the heart rate variation increase. According to the recommendations of the Finnish Institute of Occupational Health, the heart rate variation should be more than 20 ms during sleep.

Night RMSSD can be classified into, for example, the classes >(good), 20-40 (moderate), 13-20 (poor), and <13 (pathological). A night RMSSD class of >40 (good) is defined on the basis of empirical data and can be double compared to the moderate level. A night RMSSD class of 20-40 (moderate) is a criterion limit for poor recovery, in other words this is the level that a person who is basically healthy should at least achieve during a normal night. Further, a night RMSSD class of 13-20 (poor), which is based on empirical data, depicts a situation, in which the operation of the parasympathetic nervous system is very low and heart rate variation scarcely appears. A night RMSSD class of <13 (pathological) refers to some disease.

C) Time Used for Sleep

The amount of sleep is individual, but the following are nominal values for a sufficient amount of sleep. According to research, 10-15% of people sleep continually for less than 6 h without, however, suffering from any kind of lack of sleep. On the other hand, there is also research showing that too long sleep (>9 h) is detrimental to health. The time used for sleep can be classified, for example, into the classes >7 h (good), 5.5-7 h (moderate), and <5.5 h (poor).

D) Recovery During Leisure and Work

During the day, a person should have recovery in connection with recovery periods and breaks. If the body does not recover when possible, the loading risk may increase. Recovery during leisure and work can be classified in, for example, the following classes >60 min (good), 16-60 min (moderate), and 0-15 (poor).

E) Night RMSSD Level Relative to that Measured During the Day (States 1-4)

RMSSD should be higher at night than during the day, so that the operation of the parasympathetic nervous system will increase when resting at night. If there are disturbances in the operation of the autonomic nervous system, the RMSSD may increase randomly during the day, due for example to additional heartbeats, and remain in turn low at night when there are not the same number of additional heartbeats.

F) Number of States During the Day Interpreted as Exercise

This state is classified, if during the day many states are interpreted as exercise and 6 or 7 states are suspected of being overload states. Naturally, the classification is also affected by the content of the period, because training sessions of 2-4 h are entirely possible. An increased heart rate level can for its part also indicate an acute emergency state prevailing in the body. The classification can be, for example, 0-2 h, 2-4 h, and >4 h.

G) Relative Amount of Recovery During Sleep

This variable depicts a general loading risk. If the body does not rest at night when there should be recovery, the loading risk has increased. The values of the variable can be classified, for example, into the classes 75-100% (excellent), 50-75% (good), 25-50% (poor), and 0-25% (bad).

H) How Rapidly Recovery Appears after Sleep has Started

This variable depicts the general loading risk. Generally, beginning loading appears precisely first all in the early night. If recovery does not begin effectively immediately, the loading risk may have increased. The values of the variable can be classified, for example, into the classes >30 min (poor), 5-30 min (moderate), and 0-5 min (good).

I) Amount of Recovery During an Entire Day

The variable reflects the equilibrium relative to recovery over an entire day. The values of the variable can be classified, for example, into the classes >30% (excellent), >25% (good), 20-25% (moderate), and <20% (poor). The good recovery limit of 25% is achieved already when there are at least 6 h of recovery during sleep at night.

J) Amount of Stress Reaction States During a Day

The values of this variable can be classified, for example, into the classes <50% of the day (good), 50-65% of the day (moderate), and >65% of the day (poor).

K) Amount of Unidentified States During a Day

The amount of unidentified states consists of three different factors and this, for its part, affects the interpretation. The different factors can be a lack of a signal or a disturbance, a state after exercise in which EPOC and VO2max are increased, or an unidentified state, in which case the heart rate is slightly increased, but does not yet correspond in stress to the level of everyday exercise. This variable can be classified into, for example, the classes 0-2 h (little), 2-6 h (moderate), and >6 h (much).

L) Return of the resourceVector to at Least its Initial Level in Daily Measurements A result exceeding the initial level generally occurs already at a 20-25% recovery share.

In the state matrix used in the method, points are calculated for each physiological state, with the state receiving the most points being selected as the state of the measurement. In the state matrix, the context variables, which are used to identify the states, are shown in the first column. All the context variables that can affect the states, or which are referred to in connection with some state, are listed.

Some of context variables and states collected by the expert can be left out, if overlaps are noticed empirically with the aid of the material. In that case, two or more context variables correlate strongly to each other, in other words, if one is 'on' then so is the other. FIG. 5 shows a correlation matrix depicting overlaps.

Two forms can be distinguished in the logic used in the method: AND logic, in which a specific state requires specific context variables, and a more flexible logic. The more flexible logic uses context variables in such a way that they are given points, so that AND logic can also be implemented by giving suitable points. The points are summed and when a specific threshold is passed the state can be regarded as having been identified. Thus, the AND logic can be formed in such a way that, in the threshold value, the sum of the positive amounts of points must be precisely as many points as it is possible to obtain.

In addition to the measurements measuring a physiological state, the person being examined can also be requested to fill in a preliminary-information form, in which the person evaluates subjectively their own state of health. The questions on the preliminary-information form can be used to exclude some state. For example, if the test person has stated that they are stressed (on a scale 1-5, the person has entered 4 'I feel stressed' and 5 'I often feel very tired'), it may not necessarily be sensible to produce the state 1 ('Good recovery') and its recovery expressions. If the replies of the preliminary-information form are not used in state identification, there is reason to pick out selected data from the preliminary information for the report and the analyser, especially if the conditions set for the state are not met. Such a case can be, for example, if good recovery is ascertained, but the preliminary-information form gives contrary information. The replies of the preliminary-information form can also be given points, so that they are not exclusive.

In the preliminary-information form there are also performance values. If the performance values are not met, it will then be best to print the reply/replies in question in the report, so that they will be noted in the feedback. One possible form of implementation is identified, but if there are contradictory replies in the preliminary-information form the replies are printed in the report along with the state in question, and are thus shown to the analyser.

The form to be filled beforehand can be a form to be filled with the aid of a web link, for example on the service provider's website. Thus the preliminary-information form can be used to aid interpretation and, in addition, matters, which are also important when interpreting measurement, can be picked out of it into reports. Similar forms already exist in an electronic form in various services and the number of alcohol units, for example, can be obtained from them.

The method can also include a questionnaire on sleep quality. A sleep-quality questionnaire in, for example, an electronic form can also be added to the material and scaled as a context variable in the logic.

In the method, an opinion can be given on variation in a variable being measured, for example the quality of heart rate variation. For example, the person may have a high heart rate variation during the day and/or at night, because there are many additional heartbeats in the heart rate. Another possibility is to calculate, for example, RMSSD directly only from stable heartbeat interval ranges, so that the purity of the RMSSD in interpretation will be more reliable.

The method can be tested by measuring people over a long period, so that the long-term behaviour of the states can be seen. The states should not change substantially over a short period (for example, one week), but trend changes may take place over a longer time.

Because a probability can be calculated for each state, the correlation between the states can also be analysed empirically. In states 7 and 8, the correlation becomes positive relative to the first states. The heart rate variation of the person being examined begins to be so small at both the micro and the macro levels that the state identification produced by the method will find an unidentified state, exercise, state, or rest from the measurement period, but discrimination no longer exists. In state 8, the most important distinguishing factor is a pathologically lowered RMSSD while in state 7 it is a high number of states interpreted as exercise over the measurement period.

The result of the method can be regarded as only a definition of a state, but preferably not only a state, but also feedback statements and suggested measures to improve the state, given to the person being examined. Though there can be 6-20, preferably 8-10 physiological states defined using the method, the feedback given to the person being examined can be simplified into, for example, a three-step scale. In this connection a so-called traffic-light model can be used, in which for example in the case of physiological states 1 and 2 the person being examined is shown a green light, i.e. everything is as it should be. In the case of state 3-5 a yellow light is shown, i.e. there is reason to make changes in lifestyle, and in the case of states 6-8 a red light is shown, when there is reason to make big changes in lifestyle. In addition to this, an assessment of reliability can be combined with the feedback model, in which case for example a person who has received a state 2 with low reliability is shown a yellow light.

The report shown in FIG. 7 is one possible example of the report given to the user as a result of the method. In it, a report is printed for the user of the method, i.e. a physiological expert, which summarizes the result of the method. The report can consist of, for example, blocks of background information, 143, automatic state identification and additional information 144, and a 'to-be-taken-into-account' portion 145. In the case of the background information 143, the personal information given by the person being examined and specific measurement results, such as rest heart rate, can be presented. Block 144 presents the result of the method, what the physiological state of the person has been on each day of measurement. In this example three days have been examined. Portion 140 presented a symbol and its colour depicting the quality of sleep. Different colours depict different states, which are explained lower down in portion 146. Portion 141 shows the person's physiological state identified on each day. For its part, portion 142 shows an estimate of the reliability of the state data.

The following is one example of the feedback expressions corresponding to each state and the measures for each identified state. A depiction of the state can also be attached to the feedback expression. The following are only examples of various states, their depictions, and the feedback to be given to the person being examined.

1. 'Good Recovery'

Night is mostly recovery, the heart rate variation reacts normally. Recovery also appears during the day. As feedback, the test person can be told, for example, the following: the relation between loading and recovery is in equilibrium. A certain number of stress reactions is a normal part of everyday life and short-term stress can even improve performance. Regular exercise and healthy nutrition are also an essential part of coping and overall well-being. No risk of long-term loading.

2. 'Good Recovery, but a Lack of Daytime Recovery'

The difference from state 1 is a lack of daytime recovery. As feedback, the test person can be told, for example, the following: recovery appears sufficiently during sleep, but during the day it scarcely appears at all. Daytime breaks are important, as they recharge batteries for the rest of the day and support good-quality sleep. For this reason, it is recommended to make a habit of taking regular breaks to catch your breath, in addition to sufficient sleep. Taking breaks often needs to be learned actively, as otherwise they can be easily forgotten when you are busy. It should be noted that the lunch break does not necessarily appear as recovery in the stress and recovery curve, because the start of digestion is a physiological stress as the body digests the food to make energy. What is important is that even on a busy day you should take regular and unhurried meal and coffee breaks. During the workday, even a short moment of recovery is positive.

The suggested measures for promoting the recovery of the test person can be, for example, the following:

take unhurried coffee and meal breaks. Breaks are important moments for recharging batteries;

short exercise breaks stimulate body and soul;

ensure fluid equilibrium during the day, in physical work and busy periods the need for fluid is increased;

close your eyes and relax for a moment—after a few minutes you will feel refreshed;

laugh and have fun with your colleagues—it will stimulate you!

make a realistic timetable, leave a margin for timetables to stretch, during leisure time, for example relaxation exercises, short naps, and reading promote recovery, spend time with your family, friends, and relatives.

3. 'Moderate Recovery, but Nighttime Sleep is Short'

The share of recovery in the totality is poor or moderate due to too little nighttime sleep. The nighttime resource balance and heart rate variation are good (or at least moderate, but not poor). A typical example of such a person is someone who is fit and active, but who sleeps too little. As feedback, the person can be told, for example, the following: sufficient, good-quality nighttime sleep helps to recover resources used during the day and is thus the foundation of health and coping. During sleep, the body's ability to function returns, physical tiredness goes away, and things learned are recorded in the permanent memory. When a person has slept well and sufficiently, their mind is bright and they are in a good mood. The average need for sleep is at least 7 h each night. Too little sleep can lead to weight gain and predisposes to many illnesses. Too little sleep and excessive consumption of alcohol also predisposes to depression.

A measures suggestion for the test person could be, for example, the following: try to go to bed in time, so that you will be able to sleep sufficiently. Insufficient nighttime sleep increases the importance of daytime recovery. It is then a good idea to try to take a longer break or a nap, so that the brains and body can recover sufficiently.

4. 'Delayed Nighttime Recovery'

Initial sleep is poor, but resources have recovered by morning. Recovery is moderate during work, during the day, and in total. The nighttime resource balance and heart rate variation are reasonable. There is less leeway. As feedback, the test person can be told, for example, the following; daytime loading factors often affect the body to be overstimulated during the early night. The initial-sleep stress reactions can be explained, for example, by energetic exercise late in the evening, by alcohol, a busy day, or by an intense sauna session.

Measures suggestions for improving the quality of sleep of the test person can be, for example, the following:

avoid intense exercise or physical work late in the evening, relax your thoughts before going to bed. Mental loading, for example thinking about work, reading email, or trying to resolve human relations can raise the stress level, try to go to bed in time, so that you can sleep sufficiently (about 7-9 h), loading increases the need for sleep, so that when needed try to have more sleep, to fall asleep, use well-tried means to relax, for example, reading a book, listening to music, making love, be aware that alcohol reduces sleep quality significantly, both at one time and when used repeatedly, avoid eating large meals before going to bed.

5. 'Poor Recovery'

A considerable number of stress reactions appear at night, but nevertheless the heart rate variation is good or moderate. Recovery in total is inadequate. There is (still) some leeway, for example good physical fitness in the background. When identifying the state, particular attention should be paid to the person's own impression of loading, i.e. the initial questionnaire: for some people the parasympathetic (RMSSD) aspect remains moderately good despite the loading situation. There is then reason to react if the person feels that they are overloaded. The difference from states 3 and 4 is that nights are now 'redder'.

As feedback, the test person can be told, for example, the following: in this stage at the very latest, you should work on recovery. There is still some leeway left, but recovery has clearly weakened. Individual days of loading here and there are not a problem, as long as you recover from them during the following days. If loading continues for longer without sufficient recovery, it may lead to problems in health. The risk of long-term loading has increased.

As feedback, the test person can be told, for example, the following:

don't give up your leisure time, set a definite limit for going home from work, limit working at home in your leisure time, this will let you work better the next day at work, during busy periods it's best to reduce other loading factors—don't burn the candle at both ends!

being involved in things that are important to you collects mental resources and promotes recovery, spend time with your family, friends, and relations, learn to say NO!

physical exercise stimulates body and soul and supports mental coping, a body that is physically fit recovers more effectively than one that is in poor condition. However, remember that hard training can also be a loading factor, during leisure, for example, practicing relaxation, daytime naps, and listening to music promote recovery. It is also good to use other forms of relaxation that suit you, be aware of the effect of alcohol on recovery. Even three units of alcohol will substantially weaken the quality of recovery.

6. 'Overloading'

Recovery is in total insufficient and the heart rate variation is poor. Night is mostly under load. As feedback, the test person can be told, for example, the following: the amount of stress is considerable and has raised the risk of long-term loading. Suggestions for measures for the test person can be, for example, the following: do something about the factors causing loading! If the measurement period is not different due, for example, to illness, it is important to find the reasons for the loading and low heart rate variation, so that measures can be targeted correctly.

7. 'Physical Overloading'

A great deal of exercise and other physiological states appear in the results. The heart rate variation and recovery are poor. The risk of long-term loading has increased. State 7 differs from state 6 in that in state 7 there is a great deal of exercise or other identified states in the state distribution, so that the amount of overall stress state in the relation decreases. If the person has a very high BMI, it will often be necessary to re-evaluate the METmax value, because the Jackson equation underestimates a person's maximum aerobic capacity.

As feedback, the test person can be told, for example, the following: if physical overloading is mainly due to significant overweight combined with poor aerobic condition, the primary measures are targeted on losing weight and improving physical fitness.

8. 'Burnout/Physiologically Deviant State'

At night there is recovery, but heart rate variation scarcely appears. The reason may be a cardiac-function disturbance, or for example powerful medication. In the case of state 8, there is reason to determine whether in the background is longer-term burnout (the so-called polar-bear stage) or possibly other diseases (for instance, disturbances relating to sugar metabolism or certain neurological diseases). Heart rate variations on both the micro and macro levels have decreased. The difference from stages 6 and 7 is that, although the state is physiologically weaker (the sympathetic nervous system is already exhausted), in this case a great deal of 'green' also appears. Thus, the state is, in an identification sense, partly close to state 1, the difference being, however, that RMSSD is very low.

A measures suggestion for the person being examined can be, for example, the following: recommend examination by a physician. In exceptional situations, recommend examination by a physician and possibly ECG measurement.

The method according to the invention is a tool for preventive health care. With its aid, among other things recovery and stress can be measured and lifestyle-related health risks can be evaluated. The aim is to design measures to promote the well being of the person being examined. The method is preferably based on the measurement of heart rate and heart rate variation. If deviations appear in the method's results, for which no cause-effect can be found, it is recommend that the person being examined arranges a visit to a doctor, in order to investigate the exceptional results. In addition, additional tests should be arranged if the person being examined has an exceptionally low heart rate variation during sleep and a high rest heart rate level, even though the person has no stated illnesses or medication and their weight index is normal.

The quality of the material affects substantially the variables derived from heart rate variations, in other words to what extent there are fewer and/or additional beats in the heart rate interval series, artefacts due to cardiac insufficiency, or other disturbing factors arising from the measurement equipment (including poor contact). The term artefact refers to heartbeat-signal error. One important criterion of the quality of the material is indeed the artefact percentage, which indicates the errors contained in the original measurement data. The artefact percentage can be estimated by computation.

However, the artefact percentage is not, as such, sufficient by itself to tell the quality of the material and the information produced from it. For example, having a shower and stopping the measuring device produces many errors in time, but these errors have no significant effect on the results of the analysis. Similarly, situations can arise more generally, in which part of the material is of poor quality (the artefact percentage increases), but the overall depiction of a day is good. Measurement error can be interpreted more precisely by examining the kind of error involved and how it could be corrected—are there indications of errors arising from the heart (additional heartbeats, sleep apnea, etc.), or when have the measurement errors occurred (if the errors are, for example, during the day, this will be of no significance in terms of the variables computed from nighttime recovery)? Thus, reasonable information can be produced on the quality of the variable/variables and/or in words about the material.

The reliability of the interpretation is affected by alcohol, chronic illnesses, and temporary illnesses. A chronic illness is a person's permanent state, making measurement impossible without the illness affecting the result, thus the measurement will be reliable despite a high artefact percentage possibly caused by the chronic illness. The use of alcohol and temporary illnesses must be dealt with using the same logic (unless the subject is an alcoholic, in which case the state is chronic). In the method, particularly when creating a summary, temporary factors (alcohol or illness) will diminish the reliability of the measurement and the weight of the measurement in mean-value measurement. However, at the micro-level a state identified on the day in question will depict the state of the person being examined at precisely that moment (for example, states 6-8).

The use of alcohol is not its own state, but is instead a factor explaining a state. The table of FIG. 5 shows a way of forming at least one index for the reliability of the interpretation, which allows various reliability factors to be combined, such as artefacts, alcohol, and illnesses. The index is given values of 0-100%. In addition, feedback statements can be added to the reliability of the interpretation, which are added to the feedback when some factor is detrimental to the reliability of the interpretation. In the case of the example in FIG. 5, the results obtained are circled and by adding the circled points together the result 30 is obtained. The percentages in the table of FIG. 5 for the reliability of the effect of the various factors are also based on empirical information.

If more than one state receives an equally large reliability for the measurement, then the state with the highest state-identification percentage is selected as the state.

Each row in the reliability matrix shown in FIG. 6 shows the reliability of a measurement relative to different states. Each row represents one measurement. It will be noted, that a measurement receives a higher reliability for states that are close to each other. Based on the table, it is possible to interpret the reliability with which the method has determined the physiological state of the person being examined.

A mean-value state is defined by creating a mean-value day from the various measurement days. The context variables of a mean-value day are calculated as a weighted mean value from the context variables of the other days. The reliability coefficient of each day's state identification is used as the weighting. The total length of the measurement is not used as the length of the measurement, but the times of day that are covered in total by the measurement (maximum 24 h). In other words, if the first measurement is performed over the period of time 05:00-22:30 and the second 06:00-23:00, the total period of time covered will be 05:00-23:00 (18 h).

It should be noted that using alcohol on a specific measurement day will considerably lower the weight of that day for the mean-value day, so that alcohol is not given a mean value as a context variable, but instead alcohol use is taken into account in the weighting. Once the mean-value day has been formed, it can be analysed similarly to the individual days.

In the preliminary-information form, a questionnaire generally approved in scientific research can be used. Along with the preliminary-information form, the method can include an interview between an expert and the client, which the preliminary-information form supports. The limits of the use of alcohol can also be sought from general sources. Smoking increases the heart rate after smoking while the heart rate level of regular smokers rises. This too can be taken into account in the preliminary-information form. In addition, a more general survey of lifestyle of the person being examined can be performed.

The person being examined can also be given other information in addition to coping with work and stress management, for example, general recommendations on exercise. Subjective information (the preliminary form) can be presented to the person, if it differs from the profile of the state.

There are situations, in which the person being examined is moving towards a poorer state, but due to the person's background (sportsperson, young person) changes are not yet visible in the HRV analysis in a way that they could be distinguished. If the situation (for example, work-based stress) continues, the changes will begin to become more apparent. In that case, subjective feelings (preliminary-information form and interview) should be emphasized in place of objective data (measurement and state identification).

It should be noted that gross overweight, BMI 30, or underweight, BMI 17, can also affect interpretation of the heart rate analysis. Therefore this information can also be taken into account when providing feedback. Significant overweight can easily lead to rise in heart rate in the course of a workday, appearing as light exercise or stress. Subjective information and expert information can be used to test the automatic method and to iterate the empirical values and coefficients.

The following shows one example of the use of the method on a person being examined. In the example case, the subjective feeling (preliminary-information form) of the person and state obtained (objective), shown in FIG. 8, are mutually contradictory. The reason is revealed as heavy alcohol consumption during the measurement in question.

By means of the method, the physiological state of the person has been identified as state 6 i.e. 'Overloaded'. Total recovery is insufficient and the heart rate variation is poor. Night is mostly loaded. The state points relative to the maximum number of points for the states 1-8 are: −46/29 −36/29 −11/19 −12/18 −5/13 14/18 0/28 0/23. In the preliminary-information form, the following replies appear, which are in contradiction with the identified state:

I feel stressed: value=2; Disagree somewhat

My days include moments of recovery and breaks: value=4; Disagree somewhat

I think I sleep enough: value=4; Agree somewhat

I feel I am fit at the moment: value=4; Agree somewhat

Context variables, which are in contradiction with the identified state, also appear in the state matrix:

Recovery (state 6) appears at the latest one hour after going to bed.

The reliability index of the measurement is calculated as 35% (=10%+15%−40%+30%+20%). The person being examined has drunk a great deal of alcohol (10.0 units). FIG. 8 shows the preliminary-information form that the person has filled.

The method according to the invention can be implemented using a computer program on a personal computer, in a heart rate monitor, in an ECG or pulse-measuring device such as a pacemaker, or some other fitness device, which the person being examined can easily carry with them. Generally, the implementation consists of a processing unit, a terminal device, software, and at least one device for entering data. The method is particularly suitable for determining the physiological state of adults.

Figure 9:
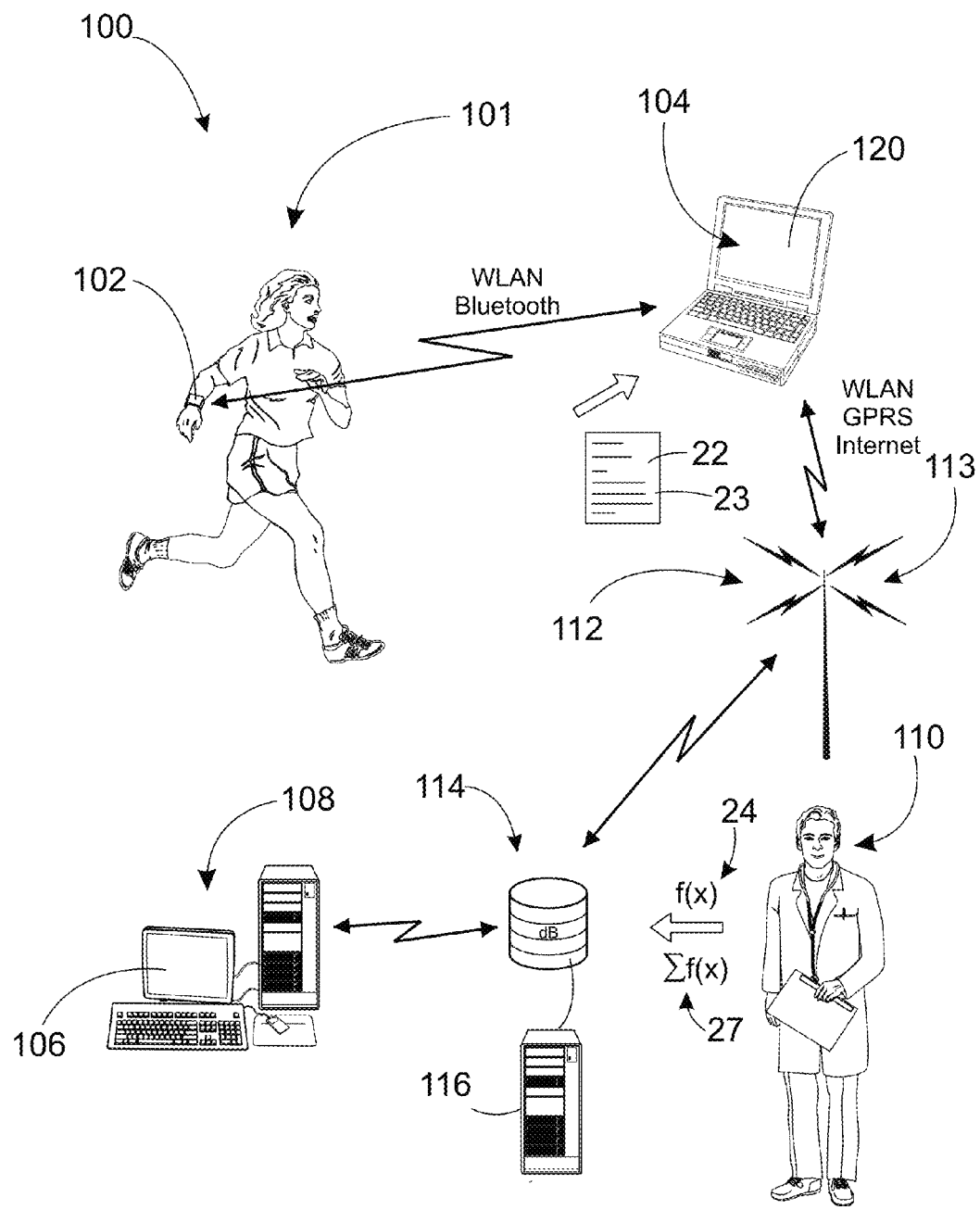
FIG. 9 shows a simplified hardware diagram of the system according to the invention.

FIG. 9 shows in a simplified form one manner of implementing the system according to the invention. The system 100 includes a mobile measuring device 102, a computer 108 for the user 110 of the system comprising software means 114 and a user interface 106, means 104 for collecting background data on the person 101 being examined comprising a second user interface 116, a data-transfer network 113, and a server 116. The software means 114 belonging to the computer 108 comprise preselected correlation functions, a preselected sum function, and reference means (not shown in the figure).

For measurements to be performed on the person 101 being examined, the person 101 has available a mobile measuring device 102, which can be, for example, a heart rate monitor, an acceleration sensor, or some other similar device, which measures a variable providing essential information on the person's state of health. The mobile measuring device 102 should be portable, so that the person 101 can use the mobile measuring device 102 in all everyday routines. In the mobile measuring device, there is preferably a memory, in which the data on the variable measured is recorded. The mobile measuring device 102 includes means, by which the recorded measurement data can be forwarded, for example, to the means 104. The means 104 are preferably a computer 104 or smart phone.

The transfer from the mobile measuring device 102 to a computer 104 can take place, for example, over a USB cable or wirelessly over a WLAN link, by Bluetooth, or using IR technology. The mobile measuring device can also include a transmitter utilizing GPRS or another similar cell-radio network, with the aid of which information can be forwarded directly to the user 110 of the system, without using a computer 104 as an intermediate step. The means 104 also act as an entering device for the person's 101 background data. The means 104 also include a user interface 120, with the aid of which the person 101 enters background data during the measurement period from data important to the measurement, for example, daily events in their diary.

The data recorded in the mobile measuring device 102 are preferably transferred to a computer 104, through which, for example, over an internet link the data are forwarded through the network's base station 112 to a server 116. The server 116 is connected to a computer 108 belonging to the system 100 for the user 110, which computer comprises software means 114 for analysing the measurement data. The data transferred to the server 116 can be stored on the server 116, or transferred from it to the computer 108 for storage. The software means 114 can also be located in the server 116, in which case the computer 108 will use the software means 114 remotely. The computer 108 includes a user interface 106, by means of which the software means 114 are controlled. The user 110 of the system 100 uses the user interface 106 to determine physiological states, to select contexts and context variables, and to enter correlation functions to the software means 114.

With the aid of the preselected correlation functions 24, the software means 114 are arranged to compute values for each variable 12, using the values of the variables of the correlation value in each physiological state 10. Thus, the correlation of the variable of each context relative to a specific physiological state can be computed automatically, so that this operation no longer requires the user's personal knowledge and familiarity with the relationships of the various variables to the physiological states.

With the aid of a preselected sum function, the software means 14 are arranged to compute a reference value for each physiological state by combining the correlation values of all the correlation functions computed for each physiological state. With the aid of comparison means, the software means 114 are arranged to determine a person's physiological state from the reference values by using a preselected criterion. The comparison means can be, for example, some function, which compares the reference value of each state to the maximum sum of the correlation functions of the state in question, and then the values of the states with each other. The use of a sum function and comparison means will further reduce the amount of work for the user, as the system's software means perform the determining of the physiological state automatically, on the basis of the values of the correlation functions.

The invention claimed is:

1. A method for evaluating a physiological state depicting a person's resources and representing different physiological recovery states, using a processing unit, a terminal device, software and at least one device for entering data, the method comprising:
   determining a plurality of alternatives of physiological states depicting resources wherein one physiological state from the determined alternatives depicts an actual physiological state of the person;
   selecting one or more contexts each corresponding to a temporal period for an action/state of the person;
   selecting one or more variables for each context;
   measuring and recording as a continuous measurement for at least 4 hours, containing one or more selected context;
   measuring and recording measurement-background data of the measurement;
   defining, with the recorded measurement, a value for each selected variable of the context, from at least one corresponding defined period;
   defining temporal periods for each context from the physiological information with the aid of the measurement-background data; and
   determining the person's actual physiological state by exploiting the measurement-background data and the measured values of the variable of each context using steps of;
      defining for each variable, a preselected correlation function in each physiological state to depict the relationship between each physiological state and the variables defined for each context;
      computing a value for each preselected correlation function using the values of the said variables and the period of time of the corresponding context;
      computing, with the aid of a preselected sum function, a reference value for each physiological state by combining the values of all the computed correlation functions of each physiological state;
      determining one physiological state from said alternatives as the actual physiological state based on the reference values using the preselected criterion; and
      presenting the actual physiological state depicting the person's resources.

2. The method according to claim 1, wherein the said context is one or more of the following: night, day, sleep time, exercise, recovery, work, and leisure.

3. The method according to claim 1, wherein the said variable of the context is one or more of the following: nighttime stress balance, daytime stress balance, nighttime RMSSD, daytime RMSSD, time used for sleep, recovery for work and leisure time, nighttime RMSSD relative to daytime RMSSD, daily exercise, recovery from sleep time, start of recovery when going to bed, recovery during one day, number of stress reactions in a day, unidentified state in a day, and recovery of resource profile.

4. The method according to claim 1, wherein the said preselected correlation function is a step function.

5. The method according to claim 1, wherein at least one or more of age, sex, height, weight, and activity class, are classified as personal-background data for use in computation.

6. The method according to claim 5, wherein a reliability coefficient is determined on the basis of the physiological information and measurement-background data, and/or the said personal-background data.

7. The method according to claim 1, wherein the person's subjective estimate of their physiological state is collected as measurement-background data, on the basis of which subjective estimate, reliability coefficient, and the physiological state determined on the basis of measurement are compared with each other, in order to provide feedback and counseling for the person.

8. The method according to claim 1, wherein between 6- and 20 physiological states are determined.

9. The method according to claim 1, wherein the person's actual physiological state is determined by comparing the reference value with a maximum value of the sum function of the values of the preselected correlation functions of each physiological state.

10. The method according to claim 1, wherein the person's physiological information is measured with the aid of heart rate and/or acceleration measurement.

11. The method according to claim 1, wherein the person's physiological information is measured with the aid of temperature measurement and/or positioning.

12. The method according to claim 1, wherein the method is used in an ECG/pulse-measurement device.

13. The method according to claim 1, wherein the person's physiological information is measured and recorded in normal living conditions.

14. The method according to claim 1, wherein between 1 and 10 of the said context variables are selected.

15. The method according to claim 1, wherein the person's physiological information is measured and recorded as a continuous measurement over a specific period of time, wherein the period of time is arranged to be of such a length that at least one context is detected on the basis of the measured physiological information.

16. A system for evaluating a physiological state depicting a person's resources and representing different physiological recovery states, in which system the person's physiological state is determined on the basis of a measured physiological information, the system comprising:
- a mobile measuring device for measuring the person's physiological information as a continuous measurement, which mobile measuring device further comprising means for recording the said information;
- software means for determining an actual physiological state from a plurality of alternative physiological states;
- a computer for a user of the system, comprising a user interface for entering initial parameters to the software means and for determining the plurality of alternative physiological states;
- means for collecting the person's measurement-background data, which means comprise a second user interface;
- a data-transfer network and a server for transferring the person's measurement-background data to the said computer;

wherein the software means comprising:
- a preselected correlation function for each variable in each physiological state for computing a correlation value using the values of the variables;
- a preselected sum function for computing a reference value for each physiological state by combining the correlation values of all the computed correlation functions of each physiological state; and
- comparison means for determining the person's actual physiological state from the reference values using a preselected criterion, wherein one physiological state from the plurality of alternative physiological states represents the actual physiological state of the person.

* * * * *